US009253979B2

(12) United States Patent
Sparks et al.

(10) Patent No.: US 9,253,979 B2
(45) Date of Patent: *Feb. 9, 2016

(54) METHODS OF CONTROLLING INSECTS

(75) Inventors: Thomas C. Sparks, Greenfield, IN (US);
Gerald B. Watson, Zionsville (IN)

(73) Assignee: Dow AgroSciences LLC, Indianapolis, IN (US)

( * ) Notice: Subject to any disclaimer, the term of this patent is extended or adjusted under 35 U.S.C. 154(b) by 328 days.

This patent is subject to a terminal disclaimer.

(21) Appl. No.: 13/336,316

(22) Filed: Dec. 23, 2011

(65) Prior Publication Data

US 2012/0172322 A1 Jul. 5, 2012

Related U.S. Application Data

(60) Provisional application No. 61/428,118, filed on Dec. 29, 2010.

(51) Int. Cl.
 *A01N 43/22* (2006.01)
 *A01P 7/04* (2006.01)

(52) U.S. Cl.
 CPC ..................................... *A01N 43/22* (2013.01)

(58) Field of Classification Search
 CPC ....... A01N 43/22; A01N 47/00; A01N 53/00; A01N 23/00; A23K 1/1873
 USPC .......................................................... 514/28
 See application file for complete search history.

(56) References Cited

U.S. PATENT DOCUMENTS

| 4,696,822 | A | | 9/1987 | Matsumura et al. |
| 4,808,206 | A | | 2/1989 | Smith |
| 5,202,242 | A | | 4/1993 | Mynderse et al. |
| 5,362,634 | A | | 11/1994 | Boeck et al. |
| 5,496,931 | A | | 3/1996 | Boeck et al. |
| 5,549,903 | A | | 8/1996 | Marcus |
| 5,571,901 | A | | 11/1996 | Boeck et al. |
| 5,591,606 | A | | 1/1997 | Turner et al. |
| 5,631,155 | A | | 5/1997 | Turner et al. |
| 5,670,364 | A | * | 9/1997 | Mynderse et al. .......... 435/252.1 |
| 5,670,486 | A | | 9/1997 | Mynderse et al. |
| 5,767,253 | A | | 6/1998 | Turner et al. |
| 5,840,861 | A | | 11/1998 | Mynderse et al. |
| 6,001,981 | A | | 12/1999 | DeAmicis et al. |
| 6,583,088 | B1 | | 6/2003 | Andersch |
| 6,919,464 | B1 | * | 7/2005 | Crouse et al. .................. 549/266 |
| 7,001,903 | B2 | * | 2/2006 | Andersch et al. ........... 514/229.2 |
| 7,737,122 | B2 | * | 6/2010 | Boucher et al. ................. 514/28 |
| 2004/0176424 | A1 | | 9/2004 | Sandeman et al. |
| 2007/0274924 | A1 | * | 11/2007 | Boucher et al. .................. 424/40 |
| 2009/0053271 | A1 | | 2/2009 | Giner et al. |
| 2010/0212029 | A1 | | 8/2010 | Orr et al. |

FOREIGN PATENT DOCUMENTS

| CA | 2382806 A1 | 10/2002 |
| CN | 101919391 | 12/2010 |
| EP | 0369614 | 5/1990 |
| WO | 03024223 A1 | 3/2003 |
| WO | 2006091672 A2 | 8/2006 |
| WO | 2010/101821 | 9/2010 |

OTHER PUBLICATIONS

Perry et al, Insect Biochemistry and Molecular Biology, 2008, 38, 520-28.*
International Search Report and Written Opinion for PCT/US2011/067150, mailed Sep. 26, 2012.
Elliott, Michael, et al., "Insecticidal amides with selective potency against a resistance (super-kdr) strain of houseflies (*musca domestica* L.)," Agric. Biol.Chem., 1986, pp. 1347-1349, vol. 50.
Perry, Trent et al., "Mutations in Dα1 or Dβ1 nicotinic acetylcholine receptor subunits can confer resistance to neonicotinoids in *Drosophila melanogaster*," Insect Biochemistry and Molecular Biology, 2008, pp. 520-528, vol. 38.
Roe, R.M., et al. "Mechanism of resistance to spinosyn in the tobacco budworm, Heliothis vierescens," Pesticide Biochemistry and Physiology, 2010, pp. 8-13, vol. 96.
Sanchez, David Mota et al., "Resistance and cross-resistance to neonicotinoid insecticides and spinosad in the Colorado potato beetle, leptinotarsa decemlineata (Say) (Coleopetra: Chrysomelidae)," Pest Management Science, 2006, pp. 30-37, vol. 62.
Watson, Gerald B. et al., "A spinosyn-sensitive *Drosophila melanogaster* nicotinic acetylcholine receptor identified through chemically induced target site resistance, resistance gene identification, and heterologous expression" Insect Biochemistry and Molecular Biology, 2010, pp. 376-384, vol. 40.
Product Safety Assessment, Spinosad, The Dow Chemical Company, Jun. 27, 2008, 7 pages.

(Continued)

*Primary Examiner* — Ganapathy Krishnan
(74) *Attorney, Agent, or Firm* — Yung H. Lee; Carl D. Corvin; Traskbritt, P.C.

(57) ABSTRACT

Methods of controlling insects include applying at least one spinosyn compound to a locus of a neonicotinoid-resistant insect, such as a strain of *Drosophila melanogaster* resistant to a neonicotinoid compound. The spinosyn compound may be a mixture of spinosyn A and spinosyn D. The spinosyn compound may cause up to approximately ten times increased mortality in the neonicotinoid-resistant insect compared to an insect susceptible to a neonicotinoid compound.

16 Claims, No Drawings

(56) References Cited

OTHER PUBLICATIONS

Spinetoram, Technical Bulletin, Dow AgroSciences LLC, 2006, 12 pages.
International Preliminary Report on Patentability for PCT/US2011/067150, mailed Jul. 2, 2013, 5 pages.
Perry et al., "A Dalpha6 knockout strain of *Drosophila melanogaster* confers a high level of resistance to spinosad" Insect Biochemistry and Molecular Biology, Jan. 20, 2007, pp. 184-188, vol. 37 No. 2.
Orr, N., et al., "Novel mode of action of spinosad: receptor binding studies demonstrating lack of interaction with known insecticidal target sites," Pesticide Biochemistry and Physiology, Sep. 1, 2009, pp. 1-5 vol. 95, No. 1.

* cited by examiner

METHODS OF CONTROLLING INSECTS

CROSS-REFERENCE TO RELATED APPLICATION

This application claims priority from U.S. Provisional Patent Application Ser. No. 61/428,118, filed Dec. 29, 2010, the entire content of which is hereby incorporated herein by this reference.

TECHNICAL FIELD

Embodiments of the present disclosure relate to methods of controlling insects and, more particularly, to methods of controlling insects that have developed resistance to neonicotinoid compounds.

BACKGROUND

Spinosyn compounds are broad spectrum insecticides known to have insecticidal activity toward insects that are pests and cause damage to crops. Spinosyn compounds are manufactured using a fermentation process in which *Saccharopolyspora spinosa* colonies are grown using natural products, such as soybean and cottonseed meal. Neonicotinoid compounds are compounds that have been used as insecticides for over twenty years. Neonicotinoid compounds, such as imidacloprid, are one of the top selling classes of insecticides. However, over the years, insects have begun to develop resistance to neonicotinoid compounds. The development of resistance to insecticides is well known. There are estimated to be at least 400 species of arthropods that are resistant to one or more insecticides.

Insecticides affect a specific target site of the insect, such as a protein. Many insecticides acting at identified target sites are losing effectiveness due to increased resistance in field populations of the insects. Spinosyn compounds and neonicotinoid compounds are believed to act at different subtypes of nicotinic receptors. While spinosyn compounds are allosteric modulators at the nicotinic acetylcholine receptor (nAChR), neonicotinoid compounds are agonists at the nAChR. Spinosyn compounds act at a distinct site from the target site of the neonicotinoid compounds.

BRIEF SUMMARY

An embodiment of the present disclosure includes a method of controlling insects comprising applying at least one spinosyn compound to a locus of a neonicotinoid-resistant insect.

Another embodiment of the present disclosure includes a method of controlling insects comprising applying a spinosyn composition to a locus of a *Drosophila melanogaster*, the *Drosophila melanogaster* having at least one lesion in the nAChR.

Yet another embodiment of the present disclosure includes a method of controlling insects comprising applying a spinosad composition to a locus of a *Drosophila melanogaster* resistant to imidacloprid.

DETAILED DESCRIPTION

Methods of controlling insects are disclosed. The term "insect," as used herein, means and includes an air-breathing arthropod of the class Insecta that has six legs and typically one or two pairs of wings at some stage during its life cycle. The insect may be a neonicotinoid-resistant insect. As used herein, the term "neonicotinoid-resistant insect" means and includes an insect strain or population that exhibits a target site resistance to at least one neonicotinoid compound. The neonicotinoid compound may include, but is not limited to, acetamiprid, clothianidin, dinotefuran, imidacloprid, nitenpyram, thiacloprid, thiamethoxam, imidaclothiz, BYI-02960 (also known by CA name 2(5H)-Furanone, 4-[[(6-chloro-3-pyridinyl)methyl](2,2-difluoroethyl)amino]- and also known as flupyradifurone), or combinations thereof. As known in the art, neonicotinoid compounds are conventionally used as insecticides. However, some strains or populations of insects have developed resistance to neonicotinoid compounds. The neonicotinoid resistance is a relative response of genetically defined insect populations to the effects of the neonicotinoid compound. An insect strain or population is considered to be resistant to the neonicotinoid compound if the insect exhibits a reduced sensitivity to the neonicotinoid compound (assessed as the dose of neonicotinoid compound utilized to inactivate or kill 50% of a treated population or group) that is at least approximately two times greater (such as, e.g., from approximately four times to more than ten times greater) than the sensitivity of an appropriate reference or so-called "susceptible" insect strain or population.

In a particular embodiment, the method includes applying at least one spinosyn compound to the neonicotinoid-resistant insect or to an area to be protected against the neonicotinoid-resistant insect in order to control the neonicotinoid-resistant insect. As used herein, the term "control," or grammatical variations thereof, means and includes causing a decrease in the number of living neonicotinoid-resistant insects or a decrease in the number of viable eggs of the neonicotinoid-resistant insect. The spinosyn compound may be more active toward the neonicotinoid-resistant insect than toward a susceptible insect. As used herein, the term "susceptible insect" means and includes an insect lacking resistance to the neonicotinoid compound (e.g., an insect susceptible to the neonicotinoid compound). The spinosyn compound may be more active or potent toward the neonicotinoid-resistant insect than toward the susceptible insect.

The spinosyn compound may be applied to the neonicotinoid-resistant insect or to an area to be protected from the neonicotinoid-resistant insect, which are collectively referred to herein as a locus of the neonicotinoid-resistant insect. As used herein, the term "locus" means and includes an environment in which the neonicotinoid-resistant insect lives or where its eggs are present, such as the air surrounding the neonicotinoid-resistant insect, the food the neonicotinoid-resistant insect eats, or objects or materials the neonicotinoid-resistant insect contacts. The locus may include, but is not limited to, plants, soil, animals, or humans. By way of example, if the neonicotinoid-resistant insect eats or otherwise damages plants, such as crops, the spinosyn compound may be applied to plants that the neonicotinoid-resistant insect is known to eat. Alternatively, the spinosyn compound may be applied to the soil through which the neonicotinoid-resistant insect moves or to the skin of a human or an animal (e.g., domesticated animals, such as livestock or pets) infested with the neonicotinoid-resistant insect. The spinosyn compound may also be applied to other objects or materials in need of protection from the neonicotinoid-resistant insect, such as textiles, paper, stored grain, seeds, other foodstuffs, or buildings.

The spinosyn compound may be applied to the locus of the neonicotinoid-resistant insect in an amount effective to control or inhibit the neonicotinoid-resistant insect. The effective amount of the applied spinosyn compound may result in a measurable decrease in the number of neonicotinoid-resistant insects or viable eggs of the neonicotinoid-resistant insect. The effective amount may range from approximately 0.1 parts per million (ppm) of the spinosyn compound to approximately 1000 ppm of the spinosyn compound. The specific decrease in numbers of neonicotinoid-resistant insects or numbers of viable insect eggs may depend on the application rate of the spinosyn compound, the spinosyn compound used, and the species of neonicotinoid-resistant insect targeted.

In particular embodiments, the spinosyn compound may be up to approximately ten times more active or potent against the neonicotinoid-resistant insect than against the susceptible insect. The difference in activity between the neonicotinoid-resistant insect and the susceptible insect may provide an opportunity for improved insect control and resistance management. At a particular dose of the spinosyn compound, the spinosyn compound may provide an increased level of control (e.g., increased mortality) against the neonicotinoid-resistant insect compared to its effect against the susceptible insect. Alternatively, due to the potency of the spinosyn compound, a lower dose of the spinosyn compound may be used to control the neonicotinoid-resistant insect compared to the dose used to control the susceptible insect. Using a lower dose of the spinosyn compound in the method of the present disclosure may also provide a lower cost and ecological advantages.

Without being bound to any particular theory, the neonicotinoid-resistant insect's resistance to the neonicotinoid compound may be due to at least one lesion in a receptor subunit of the nAChR. As used herein, the term "receptor subunit of the nAChR" means and includes a protein that is a constituent of an intact nAChR (e.g., nicotinic acetylcholine $D\alpha1$, $D\alpha2$, $D\alpha3$, $D\alpha4$, $D\alpha5$, $D\alpha b$, $D\alpha7$, $D\beta1$, $D\beta2$, or $D\beta3$ receptor subunits, and coexpressed subunits thereof). By way of example, the neonicotinoid-resistant insect may have at least one lesion in at least one of the $D\alpha1$ and $D\beta2$ subunits of the nAChR. The lesion may be a molecular alteration of a nucleic acid relative to the parental nucleic acid from which it was derived or to the nucleic acid obtained from a wild-type population. For instance, the lesion may be a deletion, inversion, insertion, duplication, transition, transversion, or a rearrangement in a nucleic acid sequence. By way of further example, the neonicotinoid-resistant insect may have a lesion in the $D\alpha1$ subunit of the nAChR that results in the loss of the fourth transmembrane structure and an extension of missense amino acids to the protein. The neonicotinoid-resistant insect may, alternatively, have a lesion in the $D\beta2$ subunit of the nAChR, which results in the formation of a truncated protein due to a premature stop codon within the cytoplasmic loop prior to the fourth transmembrane domain. The neonicotinoid-resistant insect may also have lesions in both the $D\alpha1$ and $D\beta2$ subunits of the nAChR.

The spinosyn compound may be a naturally produced or synthetic polyketide-derived tetracyclic macrolide. The spinosyn compound may be a fermentation product including at least one of the compounds produced by *Saccharopolyspora spinosa* and disclosed in U.S. Pat. No. 5,362,634, the disclosure of which is incorporated by reference herein in its entirety. The spinosyn compounds have been referred to as factors or components A, B, C, D, E, F, G, H, J, K, L, M, N, O, P, Q, R, S, T, U, V, W, or Y, and are referred to herein as spinosyn A, spinosyn D, etc. The spinosyn compound may be a 5,6,5-tricylic ring system, fused to a 12-membered macrocyclic lactone, a neutral sugar (rhamnose), and an amino sugar (forosamine). These and other natural spinosyn compounds, including 21-butenyl spinosyn produced by *Saccharopolyspora pagona*, may be produced via fermentation by conventional techniques, which are not described in detail herein. Other spinosyn compounds contemplated for use in the method of the present disclosure are disclosed in U.S. Pat. Nos. 5,496,931, 5,670,364, 5,591,606, 5,571,901, 5,202,242, 5,767,253, 5,840,861, 5,670,486, 5,631,155, and 6,001,981, the disclosure of each of which is incorporated by reference herein in its entirety. The spinosyn compound may include, but is not limited to, spinosyn A (2-(((6-deoxy-2,3,4-tri-O-methyl-α-L-mannopyranosyl)oxy)-13-((5-(dimethylamino) tetrahydro-6-methyl-2H-pyran-2-yl)oxy)-9- ethyl-2,3,3a,5a, 5b,6,9,10,11,12,13,14,16a,16b-tetradecahydro-14-methyl-1H-as-indaceno(3,2-d)oxacyclododecin-7,15-dione), spinosyn D (2-((6-deoxy-2,3,4-tri-O-methyl-α-L-mannopyranosyloxy)-13-((5-(dimethylamino)tetrahydro-6-methyl-2H-pyran-2-yl)oxy)-9-ethyl-2,3,3a,5a,5b,6,9,10,11,12,13, 14,16a,16b-tetradeca hydro-4,14-dimethyl-1H-as-indaceno (3,2-d)oxacyclododecin-7,15-dione), spinosad, spinetoram, or combinations thereof. As used herein, the term "spinosad" means and includes a combination of spinosyn A and spinosyn D, and the term "spinetoram" means and includes a combination of 3'-ethoxy-5,6-dihydro spinosyn J and 3'-ethoxy spinosyn L.

Before administration to the locus of the neonicotinoid-resistant insect, at least one spinosyn compound may be formulated into a spinosyn composition that includes at least one spinosyn compound in a carrier. Spinosyn compositions are known in the art and, therefore, are not described in detail herein. The spinosyn compound may account for from approximately 10% by weight to approximately 90% by weight of the spinosyn composition. By way of example, a spinosyn composition sold under the TRACER® trade name, which is commercially available from Dow AgroSciences LLC (Indianapolis, Ind.), includes from approximately 44% to approximately 48% spinosad weight per volume (w/v), or approximately 4 pounds of spinosad per gallon. The spinosyn composition may be a solid or a liquid, such as a suspension concentrate, a water dispersible granule, a wettable powder, a bait concentrate, or a solid insect bait. If the spinosyn composition is a solid, the carrier may be an attapulgite clay, a montmorillonite clay, a diatomaceous earth, or a purified silicate. If the spinosyn composition is a liquid, the carrier may be a solvent, such as water, a water miscible organic solvent, a water immiscible organic solvent, or combinations thereof. Suitable organic solvents are known in the art, and, therefore, are not described in detail herein. Liquid formulations of the spinosyn composition may include a solid form of the spinosyn compound in suspension in propylene glycol, water, or other solvent. The spinosyn composition may be formulated by conventional techniques, which are not described in detail herein. The spinosyn composition may, optionally, include a surfactant, a solvent, an emulsifier, inorganic salts, synthetic or natural gums, or other conventional ingredients.

In one embodiment, the spinosyn compound is spinosad, which is formulated into a spinosad composition. Spinosad is the active ingredient in numerous spinosad compositions, which are commercially available from Dow AgroSciences LLC under a variety of trade names including, but not limited to, Audienz, Biospin, Boomerang, Caribstar, CONSERVE®, ENTRUST®, Flipper, GF-120®, LASER®, MS Superspin, Mozkill, Musdo Gold, Naturalure, Olgami, Spinoace, SPINTOR® 2SC, SpY, SUCCESS®, Syneis, or TRACER®. By way of example, the spinosad composition may include a mixture of from approximately 50% by volume to approximately 90% by volume of spinosyn A and from approximately 10% by volume to approximately 50% by volume of spinosyn D. In one embodiment, the spinosad composition includes 85% by volume of spinosyn A and 15% by volume of spinosyn D. In another embodiment, the spinosyn compound is spinetoram, which is formulated into a spinetoram composition. Spinetoram compositions are commercially available from Dow AgroSciences LLC under a variety of trade names including, but not limited to, DELEGATE®, RADIANT®, and EXALT™.

By way of example, the spinosyn compound/composition may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In a particular embodiment, the spinosyn compound/composition may be used to control pests in the Phyla Nematoda and/or Arthropoda. In another embodiment, the spinosyn compound/composition may be used to control pests in the Subphyla Chelicerata, Myriapoda, and/or Hexapoda. In yet another embodiment, the spinosyn compound/composition may be used to control pests in the Classes of Arachnida, Symphyla, and/or Insecta. In an alternate embodiment, the spinosyn compound/composition may be used to control pests of the Order Homoptera.

In another embodiment, the spinosyn compound/composition may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In yet another embodiment, the spinosyn compound/composition may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In an alternative embodiment, the spinosyn compound/composition may be used to control pests of the Order Dermaptera.

In another embodiment, the spinosyn compound/composition may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In yet another embodiment, the spinosyn compound/composition may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In a particular embodiment, the spinosyn compound/composition may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Myzus* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentiformi, Bernisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, kerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rho-*

*palosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the spinosyn compound/composition may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In an alternative embodiment, the spinosyn compound/composition may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

In another embodiment, the spinosyn compound/composition may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina.*

In a particular embodiment, the spinosyn compound/composition may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the spinosyn compound/composition may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In yet another embodiment, the spinosyn compound/composition may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

In an alternative embodiment, the spinosyn compound/composition may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the spinosyn compound/composition may be used to control pests of the Order Thysanura. A non-exhaustive list of particular genera includes, but is not limited to, *Lepisma* spp. and *Thermobia* spp.

In yet another embodiment, the spinosyn compound/composition may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae,*

*Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In a particular embodiment, the spinosyn compound/composition may be used to control pest of the Order Symphyla. A non-exhaustive list of particular sp. includes, but is not limited to, *Scutigerella immaculata*.

In another embodiment, the spinosyn compound/composition may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

In a specific embodiment, the neonicotinoid-resistant insect is a *Drosophila melanogaster* strain that exhibits resistance to a neonicotinoid compound.

The following examples serve to explain embodiments of the present disclosure in more detail. These examples are not to be construed as being exhaustive or exclusive as to the scope of this invention.

EXAMPLES

Example 1

Dosage mortality testing was conducted on four strains of *Drosophila melanogaster*. Each of the *Drosophila* strains tested had at least one lesion in one of the nAChR subunits or was a control strain lacking a lesion. The Dα1 EMS1 *Drosophila* strain had a lesion in the Dα1 subunit (a lesion in the Dα1 nAChR subunit that resulted in the loss of the fourth transmembrane structure and an extension of missense amino acids to the protein). The Dβ2EMS2 *Drosophila* strain had a lesion in the Dβ2 subunit (a truncated protein due to a premature stop codon within the cytoplasmic loop prior to the fourth transmembrane domain). The 4A4D *Drosophila* strain was a double mutant having lesions in both the Dα1 subunit and the Dβ2 subunit. The susceptible *Drosophila* strain or control *Drosophila* strain was the wildtype *Drosophila* strain in which the EMS lesions were generated, and is referred to in Tables 1-4 as the "Line 14" strain.

Screening was performed on first instar larvae with five replicates of fifty larvae per vial at each concentration to determine the susceptibility of each *Drosophila* strain to the spinosyn composition and to an imidacloprid composition. The spinosyn composition (spinosad) included 85% spinosyn A and 15% spinosyn D in a sugar solution. Stock solutions were typically made 0.1% w/v in acetone and then diluted to lower concentrations. The spinosyn or imidacloprid compositions were then applied to the insect diet, allowed to dry and then infested with the insect larvae.

The concentrations of the spinosyn composition and the imidacloprid composition were selected across a range to provide data enabling the effective dose (ED) that produces a response in 50% of the first instar larvae ($ED_{50}$) and the effective dose that produces a response in 90% of the first instar larvae ($ED_{90}$) to be calculated. After administering the spinosyn composition or the imidacloprid composition, the first instar larvae were visually monitored for mortality. Data were analyzed using Probit analysis to determine the $ED_{50}$ and the $ED_{90}$, along with upper and lower 95% limits.

The $ED_{50}$ (in ppm) and $ED_{90}$ (in ppm) are shown in Tables 1-4, along with upper and lower 95% limits. Tables 1 and 2 provide the $ED_{50}$, $ED_{90}$, and upper and lower 95% limits for the spinosyn composition. For comparison, Tables 3 and 4 provide the $ED_{50}$, $ED_{90}$, and upper and lower 95% limits for the imidacloprid composition.

TABLE 1

$ED_{50}$ and upper and lower 95% limits for the spinosyn composition.

| Drosophila Strain | $ED_{50}$ (ppm) | Lower (ppm) | Upper (ppm) | Fold resistance |
|---|---|---|---|---|
| Line 14 | 0.0302 | 0.0235 | 0.0377 | — |
| Dα1EMS1 | 0.0038 | 0.0029 | 0.0049 | 0.1256 |
| Dβ2EMS2 | 0.0249 | 0.0197 | 0.0151 | 0.8264 |
| 4A4D | 0.0224 | 0.0173 | 0.0282 | 0.7434 |

TABLE 2

$ED_{90}$ and upper and lower 95% limits for the spinosyn composition.

| Drosophila Strain | $ED_{90}$ (ppm) | Lower (ppm) | Upper (ppm) | Fold resistance |
|---|---|---|---|---|
| Line 14 | 0.0810 | 0.0653 | 0.1023 | — |
| Dα1EMS1 | 0.0102 | 0.0080 | 0.0131 | 0.1256 |
| Dβ2EMS2 | 0.0528 | 0.0420 | 0.0673 | 0.6518 |
| 4A4D | 0.0603 | 0.0482 | 0.0765 | 0.7434 |

TABLE 3

$ED_{50}$ and upper and lower 95% limits for the imidacloprid composition.

| Drosophila Strain | $ED_{50}$ (ppm) | Lower (ppm) | Upper (ppm) | Fold resistance |
|---|---|---|---|---|
| Line 14 | 0.14 | 0.11 | 0.17 | — |
| Dα1EMS1 | 2.91 | 2.24 | 3.56 | 20.63 |
| Dβ2EMS2 | 4.04 | 3.22 | 4.87 | 28.69 |
| 4A4D | 3.78 | 2.84 | 4.87 | 26.81 |

TABLE 4

$ED_{90}$ and upper and lower 95% limits for the imidacloprid composition.

| Drosophila Strain | $ED_{90}$ (ppm) | Lower (ppm) | Upper (ppm) | Fold resistance |
|---|---|---|---|---|
| Line 14 | 0.28 | 0.22 | 0.37 | — |
| Dα1EMS1 | 5.77 | 4.73 | 7.29 | 20.63 |
| Dβ2EMS2 | 8.02 | 6.64 | 10.19 | 28.70 |
| 4A4D | 7.49 | 5.78 | 10.34 | 26.81 |

As evidenced by the data in Tables 1-4, the spinosyn composition is nearly ten times more potent or active against strains of *Drosophila melanogaster* that exhibit target site resistance (e.g., Dα1EMS1, Dβ2EMS2, 4A4D, which had lesions in the nAChR) compared to strains of *Drosophila melanogaster* lacking the target site resistance (e.g., Line 14, which were susceptible *Drosophila melanogaster* lacking lesions in the nAChR).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of controlling insects, the method comprising:
applying a spinosyn compound to a locus of an insect having at least one lesion in at least one of Dα1 subunit and Dβ2 subunit of the nicotinic acetylcholine receptor, wherein the method achieves up to approximately ten times increased mortality in the insect having at least one lesion in at least one of Dα1 subunit and Dβ2 subunit of the nicotinic acetylcholine receptor, compared to an insect lacking the at least one lesion.

2. The method of claim 1, wherein the insect having at least one lesion in at least one of Dα1 subunit and Dβ2 subunit of the nicotinic acetylcholine receptor comprises an insect in the order of Lepidoptera, Diptera, Homoptera, Thysanoptera, Coleoptera, Anoplura, Dermaptera, Blattaria, Hemiptera, Hymenoptera, Isoptera, Mallophaga, Siphonaptera, Thysanura, Acarina, Symphyla, Nematoda, or Orthoptera.

3. The method of claim 1, wherein applying the spinosyn compound comprises applying a spinosad compound.

4. The method of claim 3, wherein applying a spinosad compound comprises applying an insecticide consisting essentially of from approximately 50% by volume to approximately 90% by volume of spinosyn A and from approximately 10% by volume to approximately 50% by volume of spinosyn D.

5. The method of claim 1, wherein applying the spinosyn compound comprises applying a spinetoram compound.

6. The method of claim 1, wherein the insect is resistant to at least one of acetamiprid, clothianidin, dinotefuran, flupyradifurone (BYI 02960), imidacloprid, imidaclothiz, nitenpyram, thiacloprid, and thiamethoxam.

7. A method of controlling insects, comprising:
applying a spinosyn compound to a locus of a *Drosophila melanogaster* having at least one lesion in at least one of Dα1 subunit and Dβ2 subunit of the nicotinic acetylcholine receptor.

8. The method of claim 7, wherein applying the spinosyn compound comprises applying the spinosyn compound to the locus of a *Drosophila melanogaster* having at least one lesion in a Dα subunit of the nicotinic acetylcholine receptor.

9. The method of claim 7, wherein applying the spinosyn compound comprises applying the spinosyn compound to the locus of a *Drosophila melanogaster* having at least one lesion in a Dβ2 subunit of the nicotinic acetylcholine receptor.

10. The method of claim 7, wherein applying the spinosyn compound comprises applying the spinosyn compound to the locus of a *Drosophila melanogaster* having lesions in a Dα1 subunit and a Dβ2 subunit of the nicotinic acetylcholine receptor.

11. A method of controlling insects, comprising:
applying a spinosad compound to a locus of a *Drosophila melanogaster* having at least one lesion in at least one of the Dα1 subunit and the Dβ2 subunit of the nicotinic acetylcholine receptor.

12. The method of claim 11, wherein applying a spinosad compound comprises applying an insecticide consisting essentially of spinosyn A and spinosyn D.

13. The method of claim 11, wherein applying the spinosad compound comprises applying the spinosad compound to the *Drosophila melanogaster* having a mutation in the Dα1 subunit of the nicotinic acetylcholine receptor.

14. The method of claim 11, wherein applying the spinosad compound comprises applying the spinosad compound to a *Drosophila melanogaster* having a mutation in the Dβ2 subunit of the nicotinic acetylcholine receptor.

15. The method of claim 11, wherein the method achieves up to approximately ten times more potency against the *Drosophila melanogaster* having at least one lesion in at least one of the Dα1 subunit and the Dβ2 subunit of the nicotinic acetylcholine receptor, compared to *Drosophila melanogaster* lacking the at least one lesion.

16. A method of controlling insects, comprising applying an insecticide consisting of from approximately 50% by volume to approximately 90% by volume of spinosyn A and from approximately 10% by volume to approximately 50% by volume of spinosyn D to the locus of a *Drosophila melanogaster* having lesions in a Dα1 subunit and a Dβ2 subunit of the nicotinic acetylcholine receptor in an effective amount to achieve up to approximately ten times increased mortality in said *Drosophila melanogaster* compared to a *Drosophila melanogaster* lacking the lesions.

* * * * *